United States Patent [19]

Cox et al.

[11] Patent Number: 5,290,294
[45] Date of Patent: Mar. 1, 1994

[54] METHOD AND APPARATUS FOR REMOVAL OF A FOREIGN BODY CAVITY

[76] Inventors: Brian Cox, 21792 Northwood La., Lake Forest, Calif. 92630; Jay A. Lenker, 996 Coast View Dr., Laguna Beach, Calif. 92651; Daniel C. Merrill, 2127 Danville Blvd., Walnut Creek, Calif. 94596

[21] Appl. No.: 839,011

[22] Filed: Feb. 14, 1992

Related U.S. Application Data

[63] Continuation of Ser. No. 510,136, Apr. 17, 1990.

[51] Int. Cl.⁵ .................. A61B 17/22; A61B 19/00; A61B 1/30
[52] U.S. Cl. ......................... 606/108; 128/4; 128/7; 604/19; 604/164; 604/264; 606/110; 606/113; 606/127; 606/128; 606/205
[58] Field of Search ............... 606/127, 128, 110, 113, 606/108, 1, 205, 209; 128/4, 6, 7; 604/19, 164, 264

[56] References Cited

U.S. PATENT DOCUMENTS

| 268,039 | 11/1882 | Merrill, Jr. ............... 606/127 |
| 612,569 | 10/1898 | Moscrop ................... 606/113 |
| 736,744 | 8/1903 | Kratzmueller .............. 606/113 |
| 870,021 | 11/1907 | Duffee ...................... 606/113 |
| 1,127,948 | 2/1915 | Wappler ................... 606/127 |
| 1,150,214 | 8/1915 | London ..................... 128/7 |
| 1,303,135 | 5/1919 | Wappler ................... 606/127 |
| 1,310,982 | 7/1919 | Davis ....................... 606/113 |
| 1,659,112 | 2/1928 | Littlejohn .................. 606/205 |
| 1,880,551 | 10/1932 | Wappler ................... 128/7 |
| 2,028,635 | 1/1936 | Wappler ................... 128/7 |
| 2,113,246 | 5/1938 | Wappler ................... 606/205 |
| 3,257,902 | 6/1966 | Hopkins . |
| 3,835,842 | 9/1974 | Iglesias . |
| 4,174,715 | 11/1979 | Hasson ..................... 606/127 |
| 4,178,920 | 12/1979 | Cawood et al. ............ 128/4 |
| 4,203,429 | 5/1980 | Vasilevsky et al. ........ 606/128 |
| 4,396,021 | 8/1983 | Baumgartner . |
| 4,423,727 | 1/1984 | Widran et al. ............. 128/7 |

(List continued on next page.)

FOREIGN PATENT DOCUMENTS

| 0633527 | 1/1928 | France ...................... 128/7 |
| 0132925 | 10/1919 | United Kingdom ....... 128/7 |
| 1547328 | 9/1977 | United Kingdom . |
| 2144638 | 3/1985 | United Kingdom ....... 606/128 |

OTHER PUBLICATIONS

American Cytoscope Makers Incorporated—The Ballenger Urethroscope pp. 73-74, 77-84.
Birkhoff, John "Natural History of Benign Prostatic Hypertrophy," *Benign Protstatic Hypertrophy* Chapter 1, pp. 5-9.
Chisholm, Geoffrey "Prostatectomy, Past and Present," *Benign Prostatic Hypertrophy* Chapter 6, pp. 35-44.

(List continued on next page.)

*Primary Examiner*—Stephen C. Pellegrino
*Assistant Examiner*—Glenn K. Dawson
*Attorney, Agent, or Firm*—Knobbe Martens Olson & Bear

[57] ABSTRACT

The present invention provides an apparatus of novel design for use in the rapid, non-surgical removal of foreign bodies from the urethra and bladder. In accordance with one aspect of the present invention, there is provided a transurethral snaring tool for encircling and ensnaring a foreign body within the urethral lumen or bladder. The snaring tool is further provided in one embodiment with an introduction sheath, suitable for housing a cystoscope lens or other viewing means, and an obturator, for the atraumatic introduction of the sheath. In accordance with a further embodiment of the present invention, there is provided a foreign body removal apparatus having additional tools to insert through the transurethral sheath, including a rigid forward forceps and a lateral grasping forceps. There is additionally provided a non-surgical method for removal of a foreign body from a body cavity.

16 Claims, 5 Drawing Sheets

U.S. PATENT DOCUMENTS

| | | |
|---|---|---|
| 4,461,280 | 7/1984 | Baumbartner . |
| 4,557,255 | 12/1985 | Goodman ............................ 128/7 |
| 4,660,560 | 4/1987 | Klein . |
| 4,732,150 | 3/1988 | Keener, Jr. ...................... 606/113 |
| 4,738,659 | 4/1988 | Sleiman . |
| 4,741,335 | 5/1988 | Okada .............................. 606/127 |
| 4,762,128 | 8/1988 | Rosenbluth . |
| 5,020,514 | 6/1991 | Heckele ............................ 128/4 |
| 5,031,603 | 7/1991 | Gautier et al. ..................... 128/4 |
| 5,057,114 | 10/1991 | Wittich et al. .................... 606/127 |

OTHER PUBLICATIONS

Mebust, et al. "Transurethral Prostatectomy" *Benign Prostatic Hypertrophy* Chapter 88, pp. 829–846.

510K Premarket Notification for the FDA in accordance with 21 CFR 807 "ASI Cystoscope Sheath Grasping Forceps and Foreign Body Loop" (Unpublished).

Storz: The World of Endoscopy, Urology and Endo-Urology, 4th Ed., pp. PCN7, URETH4, RES7, RES8, RES12, RES15, RES18.

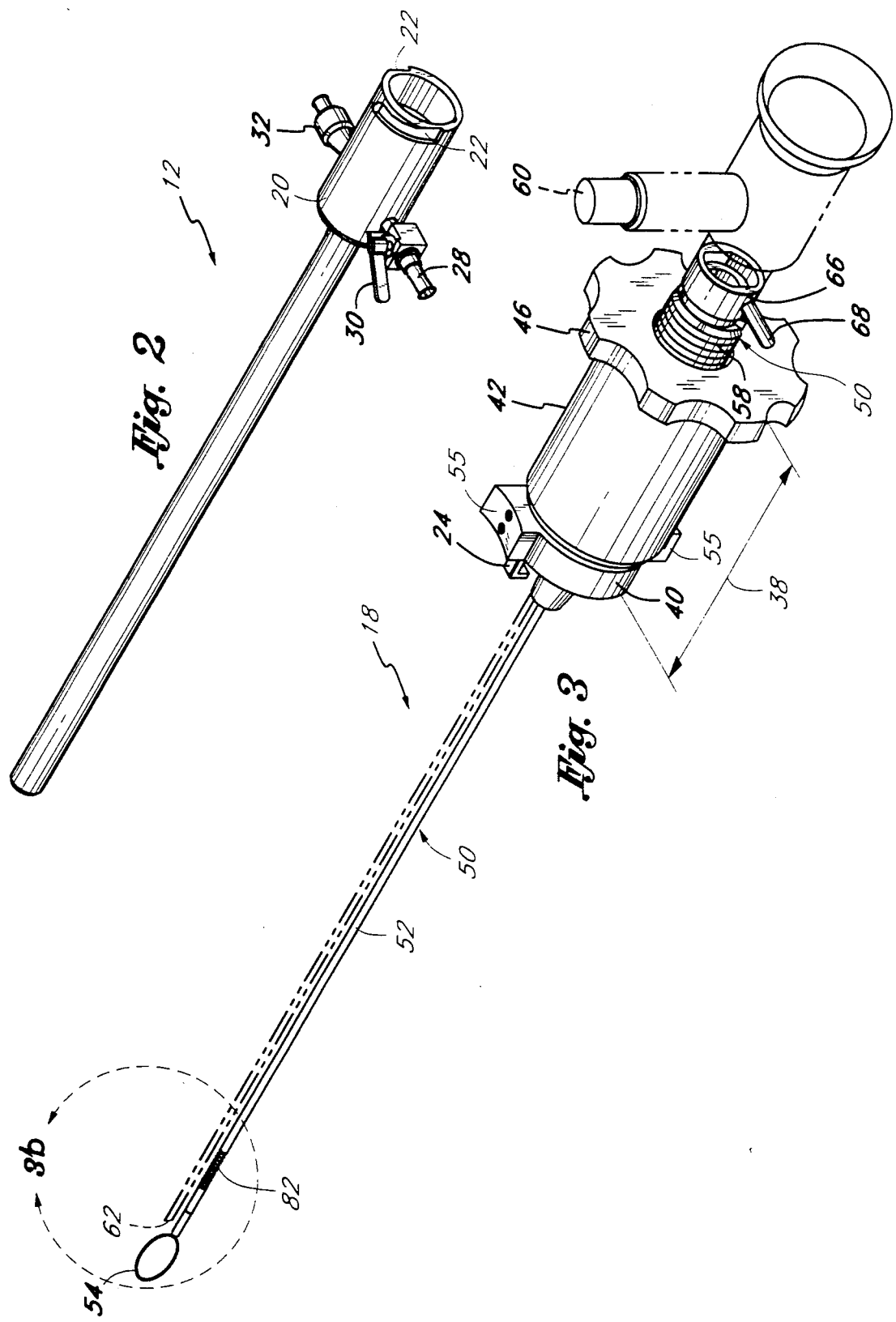

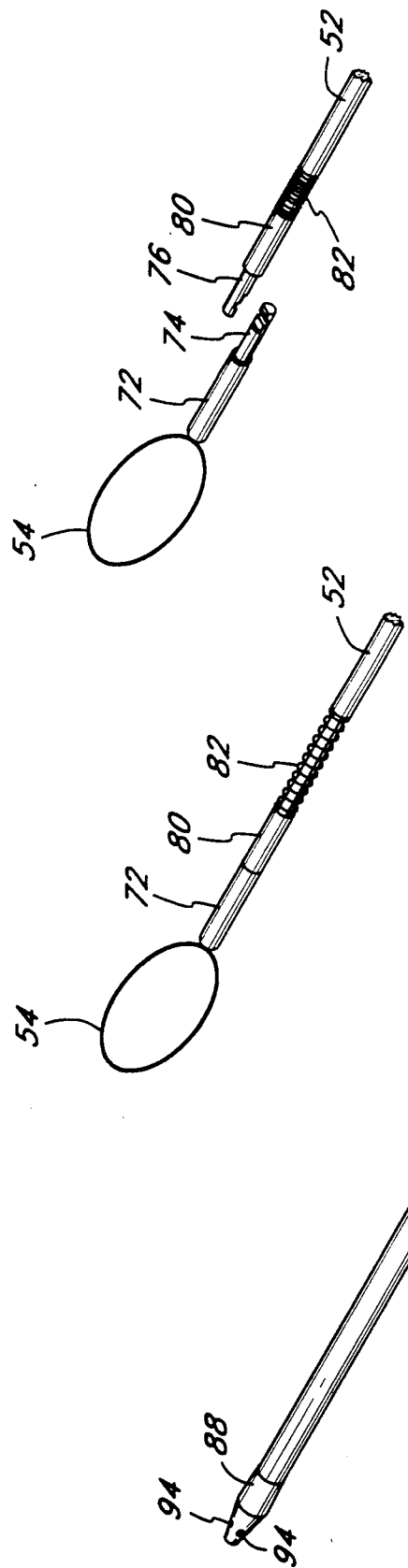
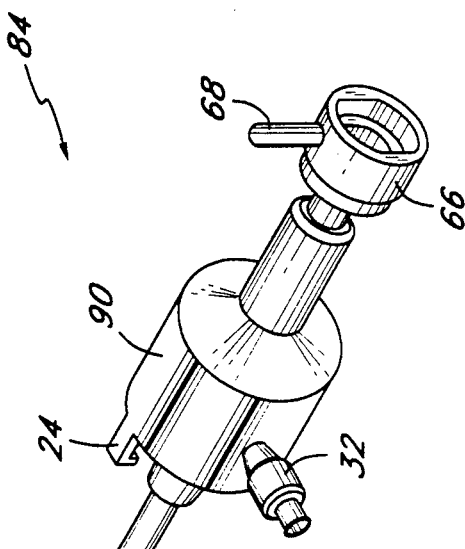

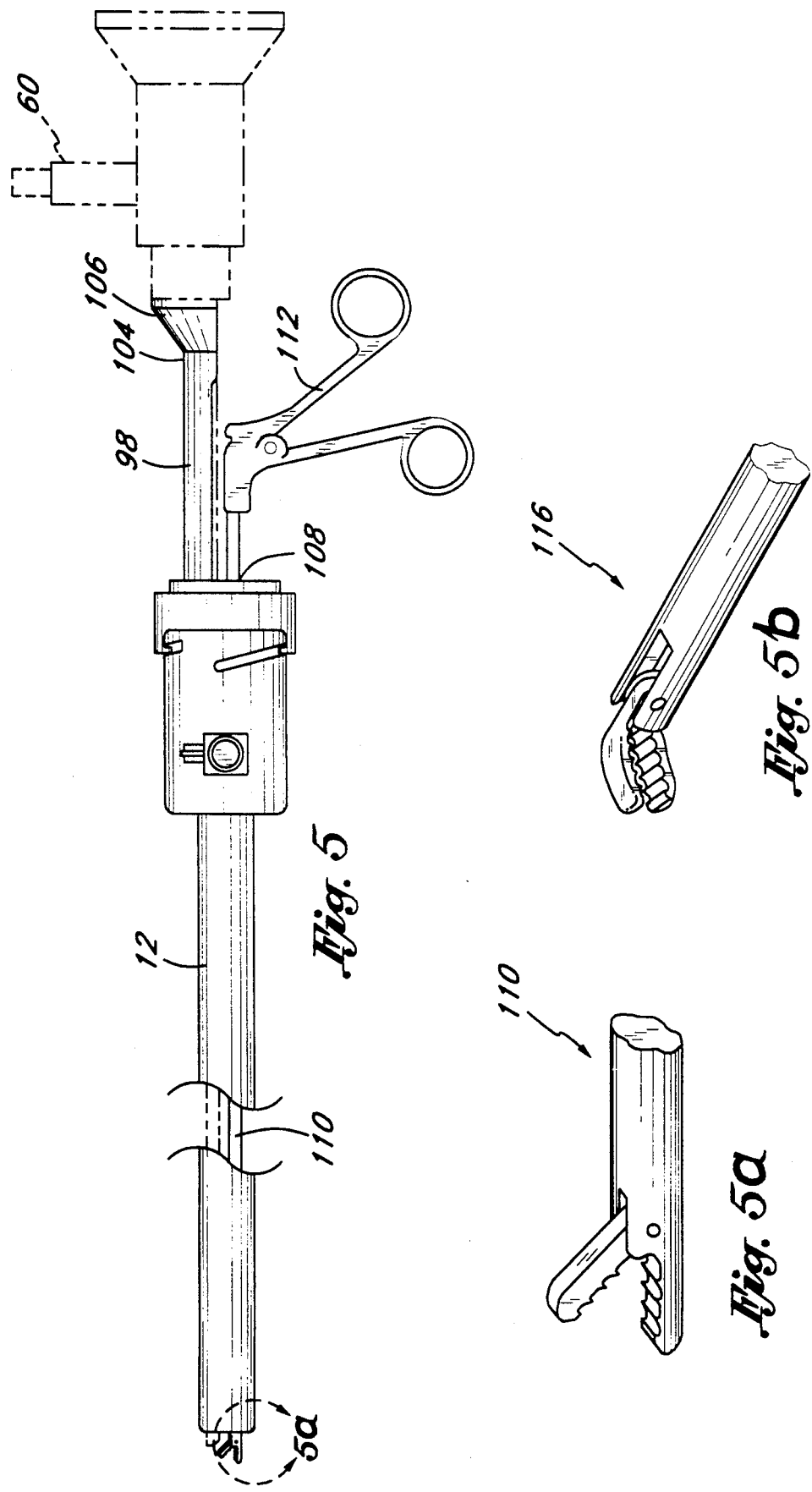

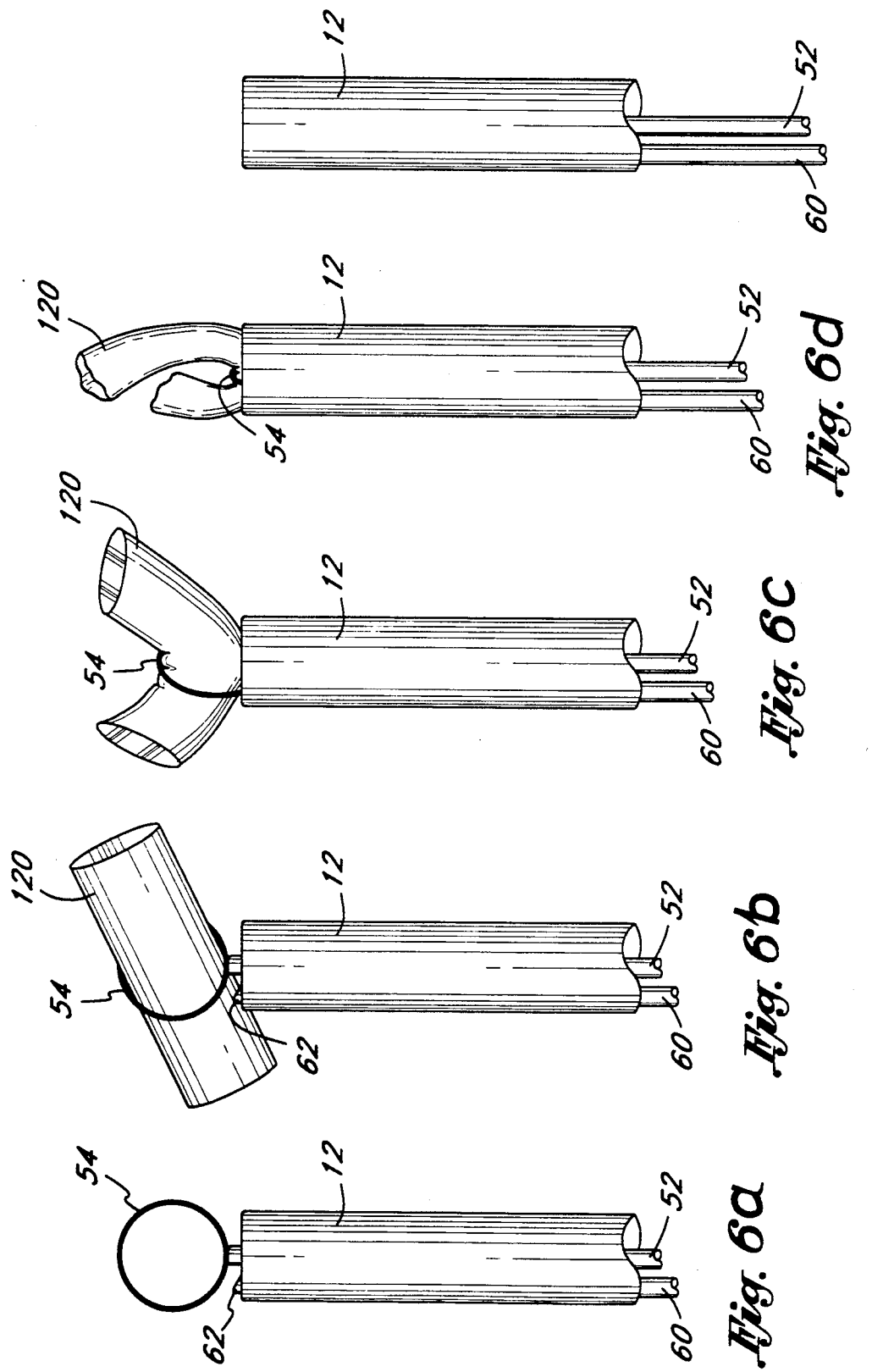

METHOD AND APPARATUS FOR REMOVAL OF A FOREIGN BODY CAVITY

This application is a continuation of application Ser. No. 510,136, filed Apr. 17, 1990.

BACKGROUND OF THE INVENTION

The present invention relates generally to the field of instruments for insertion into a body cavity. More specifically, the present invention relates to instruments which are used to remove foreign bodies from the urethra and bladder.

The prostate is a walnut-sized gland that extends around the urethral lumen from the neck of the bladder to the pelvic floor. Because of the close relationship of the prostate to the urethra, enlargement of the prostate, usually referred to as hyperplasia or hypertrophy, may fairly quickly obstruct the urethra, particularly if the hyperplasia occurs close to the lumen. Such an obstruction inhibits normal micturition, which causes an accumulation of urine in the bladder.

Various methods of treatment for hyperplasia of the prostate gland have been developed. Recently, methods of treatment have been developed comprising the steps of transurethrally inserting and positioning a tubular stent within a restricted portion of the urethra. The use of such implantable stents for dilating the urethra is disclosed in detail in U.S. Pat. No. 4,762,128 issued to Robert F. Rosenbluth on Aug. 9, 1988, the disclosure of which is hereby incorporated by reference in the present case. This method has significant advantages over previous surgical methods of treatment of hyperplasia including a significant reduction of many complications including impotence, incontinence, bleeding, infection, residual urethral obstruction, urethral stricture, and retrograde ejaculation. Accordingly, use of this method is becoming increasingly widespread.

The tubular stents associated with the aforementioned method are generally designed to remain in place indefinitely. However, removal of the stent may occasionally be required. For example, the stent may have been placed poorly, or it may have drifted out of its appropriate location. Removal of the stent may also be required if complications, such as infection, bleeding or urethral stricture, develop.

Open surgical removal of the stent whereby an incision is made to expose the stent for removal under direct vision is one option when removal of the stent is desired. However, use of such surgical methods are highly invasive and may involve significant patient discomfort, a potentially long hospital stay, and a not insignificant rate of morbidity. Therefore, such surgical procedures are, preferably, avoided.

Thus, notwithstanding the availability of surgical procedures for the removal of foreign objects from the prostatic and urethral environment, a less invasive procedure which would reduce or eliminate the occurrence of complications from surgery would be of significant value. In this regard, a procedure for entering the prostatic environment through the natural opening of the urethra would avoid the need for making an incision into the patient. It is important that such a procedure minimize trauma to the soft tissues of the urethral lining. Additionally, a means for easily locating both the object to be removed and the removal instrument would preferably be provided to minimize the time and difficulty of the procedure. Moreover, it would be desireable to have a plurality of techniques available which can be successively attempted without delay, in the event one technique was unsuccessful. The availability of a plurality of techniques would allow surgery to be used only as a last resort.

One prior art method used for the removal of foreign bodies and pieces of tissue from the urethra, bladder or other body cavity comprises transurethrally inserting a forceps through a cystoscope-urethroscope sheath, grasping the foreign body with the forceps under the vision of a transurethral telescope, and pulling the foreign body through the sheath. Such forceps, sheaths and telescopes are available, for example, from Karl Storz Endoscopy-America, Inc., Culver City, Calif. The foreign body may require substantial crushing and/or breaking in order to fit through the sheath when this prior art method is practiced. Many of the stents useful in the treatment of hyperplasia are too large and/or rigid to be effectively pulled into the sheath with the available forceps. Moreover, even where removal of the stent with these devices is possible, it is only possible with much patience and effort. It is desirable to perform these procedures as rapidly as possible, in order to avoid complications and patient discomfort. Additionally, in the event use of the forceps is not successful in removing the stent, an emergency open surgery may be necessary.

Another prior art procedure that has been used in removing kidney stones and other foreign bodies from the bladder makes use of what have come to be called stone baskets. These stone baskets are comprised of two or more flexible wires forming a "basket" into which the stone or other foreign body may be trapped. The baskets are then pulled into a transurethral sheath which is then removed. However, stone baskets are not capable of crushing kidney stones or other foreign bodies trapped by the basket. Removal of larger objects requires the use of a forceps or other tool prior to use of the stone basket to break up and/or crush any objects which will not fit through the sheath. Breaking the object into pieces, also, necessitates the removal of many pieces, taking additional time. Moreover, it may be difficult to ascertain that all of the pieces have been removed. Thus, there is a need for a more rapid and effective means for removal of foreign bodies from the urethra and/or bladder.

Cutting loops have been used in the surgical treatment of hyperplasia of the prostate and other urological conditions. These sharp, rigid prior art loops have been adapted to fit through a transurethral sheath in a non-secured fashion. The cutting loops have been used for cutting undesired tissue, however, such loops have never been adapted for the removal of foreign objects.

SUMMARY OF THE INVENTION

Briefly, the present invention provides an apparatus of novel design for use in the rapid, non-surgical removal of foreign bodies from the urethra and bladder.

In accordance with one aspect of the present invention, there is provided a transurethral snaring tool for encircling, and thereby ensnaring, a foreign body within the urethral lumen or bladder. The snaring tool has an encircling means, such as a loop, to encircle the foreign body. Advantageously, by inserting the snaring tool through the natural opening of the urethra, incision into the patient is avoided. The transurethral tool is further provided in one embodiment with an introduction sheath, suitable for housing a cystoscopic rod lens or other telescope device or viewing means, and an obturator, for the atraumatic introduction of the sheath. Preferably, the transurethral tool is provided with a means for controllably retracting the foreign body, which will pull the foreign body into the sheath. In one embodiment of the invention, a jack screw is provided as such a means of controllable retraction. The jack screw provides significant mechanical advantage, thereby allowing a user of the invention to retract the foreign body without expenditure of great force. In this embodiment of the invention, the obturator is, preferably, removed from the sheath prior to insertion of the snaring tool. The snaring tool is, preferably, adapted to receive a rod lens or other telescope device for viewing of the loop within the urethra and/or bladder.

In another embodiment, a pistol grip with a trigger ratchet assembly is used to controllably retract the snaring tool. In this embodiment, the trigger ratchet assembly functions similar to a device commonly used in caulking guns, so that each pull of the trigger further advances the ratchet to retract the snaring tool.

In accordance with a further embodiment of the present invention, there is provided a foreign body removal apparatus having additional tools to insert through the transurethral sheath. One such tool is a rigid forward forceps. This tool is useful for manipulating a foreign body within the urethra and/or bladder so that it may be removed by another tool, or may also be used to grab the foreign body and pull it through the sheath. Another tool in this embodiment of the invention is a lateral forceps which grabs from the side. The lateral forceps has been found particularly useful in shaping foreign bodies into a shape which can be easily removed by the other removal tools.

There is additionally provided a non-surgical method for removal of a foreign body from the urethra and/or bladder, comprising the steps of inserting an atraumatic sheath into the urethra, pushing the foreign body into the bladder, inserting a snaring tool of the present invention through the sheath, snaring the foreign body to be removed, and controllably retracting the object inside the sheath. The sheath may then be removed from the urethra.

The removal tools and procedures of the present invention enjoy several significant advantages. Thus, the use of the present invention significantly reduces the complications from removal of a foreign object from the urethra or bladder due to the avoidance of surgery in nearly all cases.

The provision of several removal tools and procedures which may be used without making an incision into the patient gives the user of the present invention several options before resorting to surgery. The various tools of the present invention will each fit through a single transurethral sheath which may be left in place during the changing of tools. Thus, the tools may be easily exchanged in a short period of time. All of the tools may be sterilized prior to use in a conventional manner.

The obturator provided by the present invention makes a smooth connection with the transurethral sheath. Also, the sheath and obturator tip are constructed of durable, solid, corrosion resistant material. Advantageously, the material is biologically inactive and compatible with the lining of the urethra. Thus, a smooth surface is maintained for atraumatic introduction of the sheath and obturator into the soft tissue of the urethral lining. The obturator tip has irrigation ports which allow for irrigation which further reduces trauma during insertion of the sheath.

There is no need to break objects into smaller pieces in order to make crushable objects fit through the sheath. Breaking the stent into smaller pieces is, preferably avoided because more time is required to remove all of the pieces, some of the smaller pieces are difficult to snare, and some pieces may not be seen and inadvertently not removed. The sheath being constructed of durable material allows for the foreign body to be crushed as the stent is pulled into the sheath without damaging the sheath. Thus, the foreign body is crushed to a size that will fit through the sheath during retraction of the snaring tool.

An additional advantage of the obturator tip is that it provides for a lens of the telescope device to be inserted through the center of the obturator to form a continuous smooth tip. Thus, the sheath may be atraumatically introduced with continuous viewing of the area ahead of the sheath. This viewing is particularly advantageous because it allows the user of the invention to locate a foreign object found in the urethra for pushing it into the bladder using the obturator tip. By pushing the object into the bladder, the object is placed in a larger space where it may be manipulated without causing trauma to surrounding tissue. The irrigation fluid coming through the obturator tip allows a clear view of the surrounding anatomy.

Another significant advantage of the present invention is that once the transurethral sheath is in place, the obturator may be easily and rapidly removed and replaced with a removal tool. The loop of the snaring tool is preferably flexible and constructed of metal wire. Alternatively, the loop could be constructed of coated wire, a polymer material, filament, or multi-filament. Preferably the loop has a circumference slightly larger than the object to be removed. Thus, the loop is well adapted for snaring a foreign object without tearing or cutting the object. Moreover, the tip of the snaring tool containing the loop is removable for easy replacement, yet the tip will not come apart during use of the tool. The snaring tool, like the other removal tools, is sufficiently strong to retain the foreign object as the object is pulled and crushed into the sheath. The snaring tool tip is sufficiently economical in terms of material and manufacturing costs so that it is disposed of after use, thus avoiding the possibility that the loop in the tip will deform or break due to overuse.

The jack screw, which is preferably provided to slowly and controllably retract the snaring tool thereby crushing the foreign body as it is pulled into the sheath, additionally controls the movement of the telescope device during use of the snaring tool. This provides the additional advantage that the telescope lens or other visualization means remains aligned with the tip of the removal tool as it is being retracted. Thus, the field of view remains on the foreign object being removed.

Further objects, features and other advantages of the present invention will become apparent from the ensuing detailed description, considered together with the appended drawings.

BRIEF DESCRIPTION OF THE DRAWINGS

FIG. 2 is a perspective view of the sheath.

FIG. 3 is a perspective view of the snaring tool, showing the removable loop tip thereof and the jack screw for controllably retracting the snaring tool inside the sheath.

FIG. 3a is a perspective view of the removable tip of the snaring tool showing the tip in place with the collar secured with tension from the spring.

FIG. 3b is a perspective view of the removable tip of the snaring tool shown with the collar retracted so as to allow the removal of the removable tip.

FIG. 4 is a perspective view of the obturator.

FIG. 5 is a plan view of another embodiment of the present invention showing a forward forceps tool and a telescope, in phantom, extending through the sheath with a locking bridge attached to the sheath.

FIG. 5a is a blow-up view in perspective of the tip of a forward forceps tool.

FIG. 5b is a blow-up view in perspective of the tip of a lateral forceps tool.

FIGS. 6a through 6e represent a schematic presentation of the operation of the snaring tool in accordance with a preferred method of the present invention, showing the tip of the snaring tool extending through the tip of the sheath and snaring a tubular stent which is pulled into the sheath.

DETAILED DESCRIPTION OF THE PREFERRED EMBODIMENT

Figure 1:
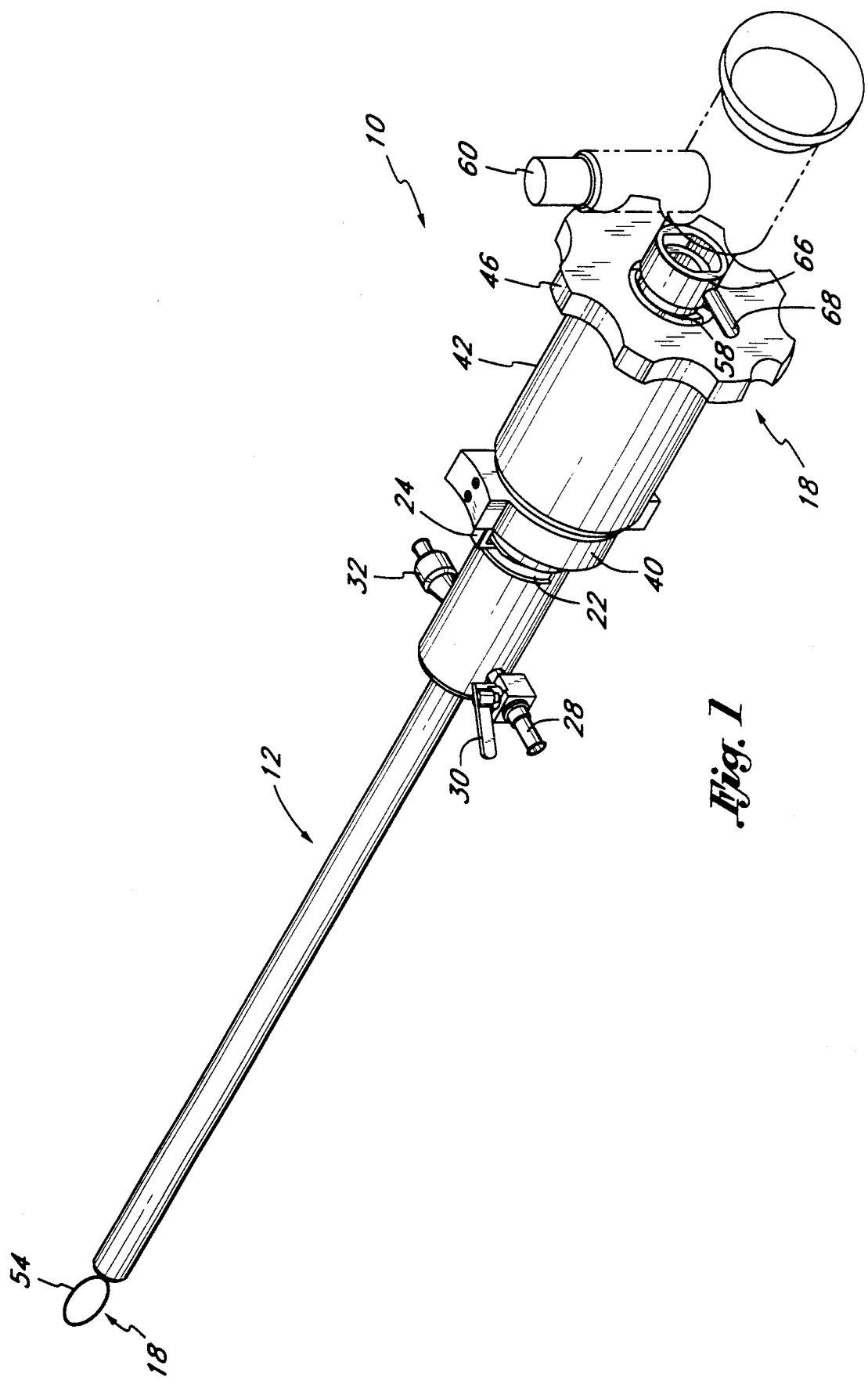
FIG. 1 is a perspective view of an apparatus for removal of a foreign body from the urethra or bladder in accordance with one embodiment of the present invention, showing a telescope in phantom.

Referring now to the drawings in detail, wherein like reference numerals designate like elements throughout the several views thereof, there is shown generally at 10, in FIG. 1, an apparatus for removal of a foreign object from a body cavity embodying the present invention in a preferred form. In this description, "proximal" will be used to refer to the end of the apparatus closest to an operator when the apparatus is in use, and "distal" will be used to refer to the end further from an operator. The apparatus, as shown in FIG. 1, has two elements, a sheath 12 and a snaring tool 18. The sheath 12, best seen in FIG. 2, is a substantially rigid tube forming an axially elongate hollow shaft throughout most of its length. Preferably, the sheath is constructed of corrosion resistant, durable, hard metal without any plating in order to maintain a smooth surface for the atraumatic introduction of the sheath into the soft tissue of the urethral lining. Advantageously, the material is biologically inactive and compatible with the lining of the urethra. Other materials, such as rigid biocompatible plastics may also be used. The provision of the transurethral sheath allows the atraumatic passage of the various tools of the present invention and of foreign bodies removed from the urethra or bladder. By providing a passageway through the natural opening of the urethra, incision into the patient is avoided.

The sheath 12 is removably locked to the snaring tool 18 or other elements of the present invention by a pair of grooves 22, cut into a cylindrical housing 20, on opposite sides thereof. The cylindrical housing 20 is disposed near the top of the sheath 12 so as to allow the elements attached to the sheath 12 to fit through the axially elongate hollow shaft of the sheath 12. In the embodiment shown, the other elements to be locked to the sheath may incorporate a pair of C-clips 24 disposed on opposite sides for locking to the grooves 22. By sliding the C-clips 24 through the grooves 22, the elements are locked together. While the embodiment shown uses a lock of C-clips 24 and grooves 22, a variety of other well known locking means are suitable for attaching the various elements of the present invention to the sheath 12. For example, any standard bayonet mount would prove suitable.

As best seen in FIG. 2, a cock valve 30 having an irrigation drainage port 28 is situated on one side of the cylindrical housing 20 of the sheath 12. The cock valve 30 allows backflowing fluids to escape the sheath 12 when positioned in the "on" position, and to prohibit the release of such fluids when in the "off" position. Situated opposite the drainage port 28 on the cylindrical housing 20 is an irrigation input port 32. In an alternative embodiment, there is only one port 28 which serves as both input and output for irrigation fluid. The ports comprise components of the irrigation system of the present invention which is described below.

The snaring tool 18 of this embodiment, as best seen in FIG. 3, comprises two component sections which move independently of each other. The non-elevating component 38 comprises an attaching means 40 with an integral jack screw key 42. The jack screw key 42 rotates freely around the attaching means 40. A jack screw handle 46, advantageously, enables the jack screw key 46 to be turned freely by an operator.

The other component of the snaring tool is the elevating component 50. The elevating component 50 comprises a narrow axially elongate shaft 52 with an encircling means, such as a loop 54, secured to its distal end. The loop 54 is preferably flexible and constructed of wire. Alternatively, the loop 54 could be constructed of coated wire, a polymer material, filament, or multifilament. The loop 54 may be immediately adjacent to the distal end of the shaft 52 as shown, or the loop 54 may be formed slightly away from the distal end of the shaft 52 to provide additional flexibility (not shown). In the embodiment of the invention having the loop away from the shaft 52, the attachment of the loop 54 to the shaft 52 may, advantageously, be a wire unitary with the loop 54; alternatively, the attachment may be a separate piece of material. The loop 54 may be coplanar with the shaft 52, or preferably, the loop 54 comes out of the plane of the shaft 52. In a particularly preferred embodiment, the loop 54 is perpendicular to the axis of the shaft 52.

The proximal end of the shaft 52 is attached to a jack screw 58 which is threaded through the jack screw key 42. Thus, an operator, by turning the jack screw key 42, will raise or lower the entire elevating component 50 relative to the non-elevating component 38. No part of the elevating component 50 rotates as the jack screw key 42 is turned. The jack screw 58 provides significant mechanical advantage, thereby allowing a user of the invention to retract the foreign body without expenditure of great force. The attaching means 40 is preferably provided with handles 55 to allow the non-elevating component 38 to be easily held in order to prevent rotation of the non-elevating component 38. Thus, the elevating component 50, including the loop 54 and any foreign body held by the loop 54 do not rotate as the elevating component 50 rises relative to the non-elevating component 38. Referring back to FIG. 1, where the snaring tool 18 is attached to the sheath 12, an operator of the embodiment of the apparatus shown will be able to extend or retract the loop 54 relative to the sheath 12 by turning the jack screw key 42. The jack screw 58 must be secure enough to pull a foreign body snared by the loop 54 into the sheath 12 along with the loop 54 when the loop 54 is retracted.

Of course, other means of controllably and securely extending or retracting the loop 54 relative to the sheath will be known to one skilled in the art. For example, a jack system operating through gears and a row of steps may be provided (not shown). In this embodiment, a pistol grip with a trigger ratchet assembly may be used to controllably retract the snaring tool 18. The trigger ratchet assembly of this alternative embodiment may function similar to a device commonly used in caulking guns, so that each pull of the trigger further advances the ratchet to retract the snaring tool 18.

The loop 54 of the snaring tool 18 is flexible and has a circumference slightly larger than the object to be removed. Thus, the loop 54 is well adapted for snaring a foreign object without tearing or cutting the object. Moreover, the loop 54 is removable for easy replacement, yet the tip will not come apart during use of the tool. The loop 54, like the grasping component of the other removal tools which are described herein, is sufficiently strong to retain the foreign object as the object is pulled and crushed into the sheath 12. The loop 54 is sufficiently economical in terms of material and manufacturing costs so that it may be disposed after use. Disposing the used loop 54 avoids the need to resterilize the tip 54 after use and additionally avoids the possibility that the loop 54 will deform or break due to overuse. Therefore, the loop 54 is preferably detachable from the shaft 52 of the removal tool 18 for rapid replacement. Used loops are preferably disposed after a single use because the loop 54 may tend to deform after each use.

FIGS. 3a and 3b show one embodiment of a system for the rapid replacement of the loop 54. In the embodiment shown, the loop 54 is integral to the tip piece 72. The tip piece 72 is held in place by a locking mechanism. In a preferred embodiment, the locking mechanism is a spring loaded collar 80, as seen in FIG. 3a. The tip piece 72 incorporates a hook 74 at its proximal end which is adapted to fit into a similar hook 76 at the distal end of the shaft 52. A spring-loaded collar 80 is pulled down in order to expose the hook 76 on the shaft. The collar securably holds the tip piece 72 on the snaring tool 18 during use. When the hooks 74, 76 are connected, the collar 80 is released, and the spring 82 keeps the collar 80 secured over the two hooks 74, 76, as best shown in FIG. 3b.

A viewing means 60 is provided to enable an operator to directly visualize the end of the removal tool 18 and the area around it while the tool is inside a body cavity (not shown). In the embodiment shown in FIG. 1, a telescope 60 is provided as viewing means. A variety of telescopes which are useful as viewing means in this application are disclosed in U.S. Pat. No. 3,257,902, issued to Hopkins, and may be obtained from Karl Storz. In the particularly preferred embodiment shown, the telescope 60 is a rigid rod lens. The telescope 60 in the embodiment shown, advantageously extends through the sheath 12 to terminate at a viewing lens 62 just below where the loop 54 of the snaring tool 18 is attached. The telescope 60, may, advantageously, be locked to the elevating component 50 of the snaring tool 18 so that the telescope 60 is retracted or extended concurrently with the loop 54. In the embodiment shown, for example, a locking port 66 is provided at the proximal end of the removal tool 18 to secure the telescope 60. A variety of other suitable locks is available, such as a luer lock. A locking port handle 68 is provided to enable an operator to easily turn the locking port 66 to secure the telescope 60. The jack screw key 42, which is preferably provided to slowly and controllably crush the foreign object as it is pulled into the sheath 12, additionally controls the movement of the telescope device 60 during use of the snaring tool 18. This provides the additional advantage that the viewing lens 62 remains aligned with the tip of the removal tool 54 as it is being retracted. Thus, the user's field of view remains on the foreign object being removed.

The irrigation system provides flushing of blood away from the lens of the telescope 60 to aid in the viewing of the tools and the foreign object to be removed. The irrigation input ports 32 are adapted to continuously receive flushing fluid, for example from a hanging container of saline, through an irrigation conduit (not shown). The flushing fluid can be supplied through the sheath 12 to flush blood away from the telescope viewing lens 62. Alternatively, the flushing fluid can be supplied through a plurality of irrigation ports along the length of an integral sheath/obturator. In this alternative embodiment, irrigation fluid also inhibits the coagulation of any blood within the urethra. If it is necessary to drain fluid during the use of the apparatus of the present invention, the drainage port 28 may be opened through the use of the cock valve 30. In the single port embodiment of the apparatus, the irrigation conduit will need to be removed prior to drainage of fluid from the port 28. Backflowing fluid will then drain, by gravity flow, and may be disposed of. Alternatively, continuous flow irrigation may be provided, whereby back-flowing fluid continuously drains through a conduit separate from the inflow irrigation conduit.

An obturator 84 is also provided for use with the present invention. The obturator 84 is designed so as to avoid trauma during the insertion of the sheath 12 through the urethra. Once the transurethral sheath 12 is in place, the obturator 84 may be easily removed and replaced with a removal tool. The obturator 84 may also be used to push foreign objects found in the urethra into the bladder. Pushing the object into the bladder is advantageous in that the object is put in a larger space, where the object can be manipulated without causing trauma to surrounding tissue. The obturator may be integral with an atraumatic sheath or, preferably, may be a removable tool which can be attached to the sheath 12. In this embodiment, the obturator 84 is removed, leaving the sheath in place transurethrally to allow insertion of tools through the sheath 12. In the particularly preferred embodiment shown in FIG. 4, the obturator is a substantially rigid, axially elongate shaft 86 with a diameter less than that of the inside of the sheath 12 throughout most of its length. Preferably, the obturator 84 has a tip 88 which is constructed of the same biocompatible material as the sheath 12. The tip 88 of the obturator, as shown, is, advantageously, a separate piece so that it may be replaced if damaged. However, a tip 88 which is integral with the obturator shaft 86 may also be provided. The obturator tip 88 makes a smooth connection with the end of the sheath 12 when it is inserted through the sheath 12 in accordance with the present invention. In the embodiment shown, a cylindrical housing 90 is provided. The housing 90 may incorporate a pair of C-clips 24 disposed on opposite sides for locking the obturator 84 to grooves 22 on the sheath housing 20. While the embodiment shown uses a lock of C-clips 24 and grooves 22, a variety of other well-known locking means are suitable for attaching an obturator of the present invention to the sheath.

A telescope 60 in the embodiment shown, extends through the obturator 84 to terminate at the viewing lens 62 at the distal end of the obturator 84. The viewing lens 62 is shaped to create an atraumatic continuous seam with the obturator tip 88. Thus, the sheath may be atraumatically introduced with continuous viewing of the area ahead of the sheath. This viewing is particularly advantageous because it allow the user of the invention to locate a foreign object found in the urethra, and thus avoid the object. The viewing is also advantageous for pushing the object into the bladder using the obturator tip 88, in accordance with a preferred method of the present invention. Moreover, the irrigation fluid flowing through the exit holes 94 in the obturator tip 88 helps reduce trauma while the object is being pushed. The telescope 60, may be locked to the obturator 84. In the embodiment shown, for example, a locking port 66 is provided at the proximal end of the obturator 84 to secure the telescope 60. The locking port handle 68 is provided to enable an operator to easily turn the locking port 66 to secure the telescope 60 to the obturator 84.

The obturator housing 90, in the embodiment shown, has an irrigation input port 32 situated on one side. A plurality of irrigation holes 94 through which irrigation fluid can exit are preferably located within the tip 88. Alternatively, irrigation slots (not shown) could be provided for the exit of irrigation fluid. Irrigation fluid flowing through the irrigation holes 94 will keep the light input free from blood and other debris to allow clear vision of the tip 88 as the obturator 84 is inserted through the urethra. Irrigation fluid flowing through the irrigation holes 94, advantageously, also serves to facilitate and reduce trauma during insertion of the obturator 84 through the urethra.

In one embodiment of the invention, additional tools are provided for manipulating a foreign object within the urethra or bladder. The provision of these additional tools allows additional non-surgical procedures to be performed in the event that removal with the snaring tool is not possible. Thus, resort to open surgery is avoided in nearly all cases because several options are provided before such surgery is required. An incision into the patient is, preferably, avoided in order to reduce the risk of complications associated with such surgery. When used in accordance with a preferred method of the present invention, the additional tools are inserted through the sheath 12 after it is placed within the urethra. The sheath 12 may be left in place as the various tools are exchanged. Thus, the tools may be easily exchanged in a short period of time. The tools are preferably used with a viewing means to allow a view of the operation of the tools within the urethra or bladder. In the preferred embodiment shown in FIG. 5, the viewing means is a telescope 60 inserted through a locking bridge 98. The locking bridge 98 facilitates control over the various components of this embodiment of the invention. In the preferred embodiment shown in FIG. 5, the locking bridge has a pair of C-clips 24 for locking to the sheath 12 as described above in connection with FIGS. 1 and 4. The locking bridge 98 provides two channels through which components may be inserted. The first channel 102 extends through the bridge element 104 of the locking bridge. The bridge element 104 terminates with a conical structure 106 which is adapted to receive a telescope 60 in accordance with a preferred embodiment of the present invention. In the preferred embodiment shown, the conical structure 106 is cut off on the inside part of the bridge in order to facilitate the insertion of a tool into the second channel 108. The bridge element 104 provides stabilization for the component inserted through it. This is advantageous in the use of a viewing means in that the field of vision is stably maintained during use of the additional tools.

The additional tool shown in FIG. 5 is a forward forceps tool 110, illustrated in position after it has been inserted through the second channel 108 of the locking bridge 98 and through the sheath 12. A detail of the distal tip of this tool is shown in FIG. 5a. The size of the forceps may vary depending on the size of the object to be removed, however, the forceps must be capable of fitting through the sheath 12. The major portion of the tool, inserted through the sheath 12 is an axially elongated shaft. The forward forceps 110 is operated through a scissors-like mechanism 112 which extends parallel to the axially elongated shaft at the proximal end of the tool. During use of the tool, the scissors-like mechanism 112 must be held closed around an object in order to snare an object. Alternatively, a means for locking the forceps may be provided. The forward forceps tool 110 has been found particularly useful in the removal of foreign bodies which cannot be easily removed with the snaring tool. The forward forceps tool 110, for example, may be used to pull a foreign object directly into the sheath 12, or it may be used to shape a foreign object for easier removal with another tool. The forward forceps tool 110 may also be used to push a foreign object out of the urethra and into the bladder, or to hold a foreign object tightly against the loop 54 of the snaring tool 18 in order to facilitate removal of an object with the snaring tool 18.

A lateral forceps tool 116 is substantially identical to the forward forceps tool 110. However, the lateral forceps tool 116 has a scissor-like mechanism which extends perpendicular to an axially elongated shaft of the tool at the proximal end of the tool. Thus, the lateral forceps tool grabs from the side as illustrated in FIG. 5b where the tip of the lateral forceps tool 116 is shown. This lateral forceps tool 116 may be used for any of the purposes the forward forceps tool 110 may be used, and additionally has been found useful in shaping a foreign object so that it may be pulled into the sheath using the forward forceps tool.

Method of Using the Apparatus

A sheath 12 as illustrated in FIG. 2 is readied for insertion through the external urethral opening by attaching the obturator 84 illustrated in FIG. 4. The obturator 84 has a smooth, tapered tip 88 with no sharp edges so as not to induce trauma while it is being inserted. A telescope 60 with a viewing lens 62 is inserted through the obturator to serve as viewing means and to complete the smooth nature of the obturator tip 88. The mild transitions from the viewing lens 62 to the obturator 84 and from the obturator 84 to the sheath 12 are instrumental in reducing damage and trauma to the tender urethral lumen during insertion of the sheath. All tools and other components may be sterilized prior to use through any well-known method such as autoclaving or disinfecting in solutions. Irrigation is provided to the irrigation input port 32 on the obturator to further facilitate the insertion of the sheath.

During insertion of the sheath 12, it is usually desired to dislodge a foreign body found in a constricted space, such as the urethra into a larger body cavity in communication with the constricted space, such as the bladder.

By dislodging the foreign body into the bladder the object is placed into a larger space. In the larger space of the bladder, the object may be more freely manipulated without causing trauma to the surrounding tissue. This is especially advantageous during the crushing of the foreign body into the sheath 12, where the foreign body may be bent and moved to the side by the crushing activity. Dislodging the object may usually be accomplished by pushing the foreign object with the obturator tip 88. If it is not possible to push the foreign object out of the bladder using the obturator tip 88, then it will be necessary to remove the obturator 84 along with the telescope 60, leaving the sheath inserted up to the location of the foreign object. The irrigation conduit is then connected to the irrigation input port 32 in the two port embodiment of the invention or the irrigation port 28 of the single port embodiment. Irrigation fluid will clear away any blood which may block the view of the foreign object through the telescope 60. The locking bridge 98 is attached and a forward or lateral forceps tool 110 or 116 may be inserted through the second channel 108, followed by the insertion of the telescope 60. The forceps tool 110 or 116 may then be used to push the foreign object into the bladder. Once the foreign object is pushed into the bladder, the locking bridge 98, telescope 60, and forceps tool 110 or 116 are removed. The obturator 84 and telescope 60 are then reinserted and the irrigation is again connected to the irrigation port 32 on the obturator 84. The sheath 12 is then inserted through the remainder of urethra.

Once the sheath 12 is inserted through the urethra and the foreign object to be removed is in the bladder, then the snaring tool 18 is attached to the sheath 12 as shown in FIG. 1. The telescope 60 is also attached to the snaring tool 18. The distal end of the apparatus will then appear as in FIG. 6a with the loop 54 at the end of the sheath 12 and the viewing lens 62 just extending beyond the sheath 12.

The loop 54 is then used to encircle the object to be removed as shown in FIG. 6b, thereby ensnaring the object. In FIG. 6b, the object to be removed is a tubular stent 120.

Once the object to be removed is ensnared, the jack screw key handle 46 (illustrated in FIGS. 1 and 3) is slowly turned in order to retract the loop 54 along with the object. As can be seen in FIG. 6c, the telescope viewing lens 62 is retracted along with the loop as the jack screw key handle 46 is turned.

Advantageously, there is no need to break objects into smaller pieces in order to make crushable objects fit through the sheath 12. Breaking an object to be removed, such as the stent 120 into smaller pieces is, preferably, avoided because more time is required to remove all of the pieces, some of the smaller pieces are difficult to snare, and because some pieces may not be seen and inadvertently not removed. The sheath 12 being constructed of durable material allows for the object to re-moved to be crushed as the object is pulled into the sheath 12 without damaging the sheath 12. Thus, objects to be removed having a diameter larger than that of the sheath 12 may be removed through the sheath by crushing them to a size that will fit through the sheath 12.

In FIG. 6d, there is illustrated a tubular stent 120 being crushed as it is pulled inside the sheath 12 through further turning of the jack screw key handle 46.

Further retraction of the loop 54 continues through turning the handle 46 until the object 120 is totally within the sheath 12, as shown in FIG. 6e. Once the object 120 is fully within the sheath, the entire assembly (that shown in FIG. 1) containing the object 120 within may be removed from the urethra and the irrigation turned off. Alternatively, the snaring tool 18 may be removed along with the object 120 prior to the removal of the sheath 12.

In the event that drainage of irrigation fluid is necessary during the use of the apparatus, the cock valve 30 on the drainage port 28 may be opened, and the fluid drained. In the embodiment of the invention having only one port, the irrigation conduit must be removed prior to drainage. Normally, the operation of the apparatus proceeds sufficiently rapidly so that this step is not necessary.

In an alternative embodiment of the method of the present invention, the object may be removed using a forceps tool alone. To remove the object with the forceps, the snaring tool 18 is detached from the sheath 12, and is replaced with the locking bridge 98. The forward forceps tool 110, followed by the telescope 60, are inserted through the locking bridge 98 and sheath 12, as irrigation continues. It may be possible to grab the object 120 with the forward forceps tool 110 and pull it through the sheath 12. Often though, this is not possible because the leading edge of the object must fit fully into the sheath 12 in order to begin to be pulled through. Moreover, the width of the forceps 110 together with the object may be greater than the inside diameter of the sheath 12, thereby preventing the object from being pulled into the sheath 12. In either event, the object may first require shaping in order to fit through the sheath 12. The forward forceps tool 110 may be suitable for this purpose in some cases, however, the lateral forceps tool 116 has been found better suited to this task. To use the lateral forceps tool 116, it is simply replaced for the forward forceps tool 110. The object is then shaped and tapered down so that at least one end of the object is small enough to fit into the sheath 12 along with the tip of the forward forceps tool 110. Then the forward forceps tool 110 is replaced, and the object is pulled through the sheath.

It will be appreciated that certain structural variations may suggest themselves to those skilled in the art. The foregoing detailed description of the apparatus and methods is to be clearly understood as given by way of illustration, the spirit and scope of this invention being limited solely by the appended claims.

What is claimed is:

1. A kit for the non-surgical removal of foreign bodies from the urethra or bladder comprising:

an introduction sheath having a substantially rigid tube forming an axially elongate hollow shaft throughout most of its length which is inserted transurethrally to allow passage of a removal tool or other objects through the urethra without causing trauma to the urethral lining, said sheath having a distal end and a proximal end located opposite said distal end;

an obturator having a radius smaller than that of the introduction sheath throughout most of its length so that it fits through the sheath, having a means for locking to the sheath and an atraumatic tip which is biologically inactive and compatible with the lining of the urethra, so as to provide for a smooth connection with the sheath when attached thereto, thereby allowing for the atraumatic introduction of the sheath when the obturator is locked to the sheath;

a transurethral snaring tool for encircling and ensnaring a foreign body within the urethral lumen or bladder, the snaring tool fitting through and locking to the transurethral sheath after introduction of the sheath and after removal of the obturator, the snaring tool having a sturdy, yet flexible, loop which extends beyond the distal end of the sheath when the snaring tool is attached to the sheath and is in its fully extended position; and a means for controllably retracting the snaring tool into the sheath without rotating the loop when the snaring tool is attached to the sheath in order to pull the foreign body snared by the snaring tool into the sheath, wherein said means for controllably retracting the snaring tool provides sufficient mechanical advantage to crush the foreign body as the foreign body is pulled into the sheath, and wherein said means for controllably retracting the snaring tool retracts the snaring tool without applying a distally directed force on the snaring tool, said distal end of said sheath having sufficient cross-sectional area so as to allow the retraction of a foreign body along with the snaring tool into said sheath.

2. An apparatus as in claim 1, additionally comprising:

a telescope fitting through and locking to the transurethral sheath, said telescope providing a visual image of the snaring tool and the adjacent region while the snaring tool is attached to the sheath, thereby allowing continuous viewing of the area in front of the loop while the snaring tool is inside the body of a patient.

3. A kit as in claim 2, wherein the obturator tip includes an opening through which a viewing lens of the telescope fits to create a continuous smooth tip when the telescope is disposed therethrough, thereby allowing continuous viewing of the area in front of the tip during the atraumatic insertion of the sheath.

4. A kit as in claim 2, further comprising at least one irrigation port communicating between the sheath and the obturator when the obturator is locked to the sheath, whereby introduction of irrigation fluid into the at least one irrigation port facilitates the introduction of the sheath and keeps blood and debris out of a field of view of the telescope.

5. A kit as in claim 2, wherein the means for controllably retracting the snaring tool is a jack screw which is connected to said snaring tool so as to allow controllable retraction of said snaring tool, said jack screw being located adjacent the proximal end of said sheath, and wherein the jack screw also controls the movement of the telescope so that the telescope remains aligned with the tip of the snaring tool as the snaring tool is being retracted so that the field of view through the telescope remains on the foreign object being removed.

6. A kit as in claim 1, wherein the loop is attached to a separate tip piece of the transurethral snaring tool and the tip piece is held in place by a locking mechanism.

7. A kit as in claim 1, additionally comprising:

a lateral forceps tool which fits through the sheath after introduction of the sheath and after removal of the obturator, for shaping a foreign body inside the urethra or bladder, so that the foreign body can be pulled into the sheath with another tool; and a forward forceps tool which fits through the sheath after introduction of the sheath and after removal of the obturator, for shaping and grabbing a foreign body inside the urethra or bladder, so that it may be pulled out of the urethra or bladder through the sheath with the forward forceps tool or other tool.

8. A method of removing a foreign body from the urethra or bladder comprising the steps of:

locking an obturator to a transurethral introduction sheath, the sheath having a substantially rigid tube with a distal end and a proximal end, said tue forming an axially elongate hollow shaft throughout most of its length, and the obturator having a radius smaller than that of the introduction sheath throughout most of its length so that it fits through the sheath;

inserting the obturator and sheath combination through the urethra whereby the foreign object to be removed is pushed into the bladder;

unlocking the obturator from the sheath and removing the obturator, leaving the sheath in place through the urethra;

inserting a snaring tool through the sheath and locking it to the sheath, the snaring tool having a sturdy, yet flexible, loop which extends beyond the distal end of the sheath while the snaring tool is attached to the sheath;

viewing the foreign object to be removed;

ensnaring the foreign object to be removed with the snaring tool;

controllably retracting the snaring tool with the snared foreign object relative to the sheath using sufficient mechanical advantage to crush the foreign body as the foreign body is pulled into the sheath, thereby crushing the foreign body and pulling the foreign body into the sheath without breaking the object into pieces and without causing reverse pressure on the snaring tool; and removing the snaring tool along with the snared foreign object.

9. A method of removing a foreign body as in claim 8, wherein the ensnaring, retracting and removing steps are performed under direct vision of the snaring tool and the adjacent region.

10. A sturdy, biocompatible kit for the non-surgical removal of a foreign body from a body cavity which is corrosion resistant and insertable into a bladder transurethrally without causing trauma to the urethra, said kit comprising:

an axially elongate hollow sheath;

an obturator having a radius smaller than that of the hollow sheath throughout most of its length so that it fits through the sheath, having a means for locking to the sheath and an atraumatic tip which is biologically inactive and compatible with the lining of the urethra, so as to provide for a smooth connection with the sheath when attached thereto, thereby allowing for the atraumatic introduction of the sheath through the urethra when the obturator is locked to the sheath;

a snaring tool having a distal end which fits through the sheath and into the bladder, the snaring tool having a loop at the distal end thereof for encircling a foreign body, wherein the loop provides sufficient strength to pull the foreign body into the sheath wherein a tip containing the loop of the snaring tool is removable and the removable tip is held in place by a locking mechanism; and a means for controllably retracting the snaring tool inside the sheath after the foreign body has been captured by the snaring tool in order to pull the foreign body into the sheath.

11. A kit for removal of a foreign body as in claim 10, wherein the locking mechanism is a spring loaded collar.

12. A non-surgical method of removing a foreign body from a body cavity comprising the steps of:
   inserting a sheath into the body cavity;
   inserting a snaring tool, having an encircling means, completely through the sheath and into the body cavity;
   viewing the foreign body to be removed;
   pushing the foreign body from a constricted space into a larger body cavity;
   encircling the foreign body to be removed with the encircling means of the snaring tool, thereby ensnaring the foreign body;
   controllably retracting the foreign body into the sheath with sufficient mechanical advantage to crush the foreign body inside the sheath without applying a distally directed force on the snaring tool; and
   removing the sheath along with the tool and the foreign body.

13. A method of removing a foreign body as in claim 12, wherein the step of pushing the foreign body into the larger body cavity is done with an obturator.

14. A method of removing a foreign body as in claim 12, wherein the step of pushing the foreign body into the larger body cavity is done with a forceps tool.

15. A method of removing a foreign body from the urethra or bladder comprising the steps of:
   inserting a sheath into the urethra;
   inserting a lateral forceps tool into the sheath;
   viewing the foreign body while shaping the foreign body with the lateral forceps tool into a shape which will fit through the sheath along with a forward forceps tool;
   removing the lateral forceps tool and inserting a forward forceps tool into the sheath;
   viewing the foreign body to be removed;
   grabbing the foreign body with the forward forceps tool;
   controllably retracting the foreign body into the sheath by retracting the forward forceps tool to crush the foreign body inside the sheath; and
   removing the sheath along with the tool and the foreign body.

16. A method of removing a foreign body from the urethra comprising the steps of:
   inserting an introduction sheath having a tube forming an axially elongate hollow shaft with a diameter smaller than the longest diameter of the foreign body to be removed which is inserted transurethrally and which is sufficiently rigid to crush the foreign body as it is pulled inside the tube;
   pushing the foreign body from the urethra into the bladder;
   inserting a snaring tool through the sheath and into the bladder;
   viewing the foreign body to be removed;
   ensnaring the foreign body to be removed with the loop of the snaring tool;
   controllably retracting the foreign body ensnared by the snaring tool into the sheath with sufficient mechanical advantage to crush the snaring tool inside the sheath, thereby crushing the foreign body; and
   removing the sheath along with the tool and the foreign body.

* * * * *

UNITED STATES PATENT AND TRADEMARK OFFICE
CERTIFICATE OF CORRECTION

PATENT NO. : 5,290,294
DATED : March 1, 1994
INVENTOR(S) : Brian Cox, et. al.

It is certified that error appears in the above-indentified patent and that said Letters Patent is hereby corrected as shown below:

Column 14, line 11 delete "tue" and insert therefor --tube--.
Column 14, lines 37-38, delete "causing reverse pressure" and insert therefor --applying a distally directed force--.

Signed and Sealed this

Eleventh Day of October, 1994

Attest:

BRUCE LEHMAN

Attesting Officer

*Commissioner of Patents and Trademarks*